United States Patent [19]
Jacobs

[11] 4,382,438
[45] May 10, 1983

[54] INSTRUMENT FOR TREATMENT OF SPINAL FRACTURES, SCOLIOSIS AND THE LIKE

[75] Inventor: Rae R. Jacobs, Kansas City, Kans.
[73] Assignee: Synthes AG, Chur, Switzerland
[21] Appl. No.: 241,557
[22] Filed: Mar. 9, 1981
[51] Int. Cl.³ .............................................. A61F 5/01
[52] U.S. Cl. ................... 128/69; 128/92 EA
[58] Field of Search ............... 128/69, 92 R, 92 E, 128/92 EA, 92 B, 92 EC

[56] References Cited

U.S. PATENT DOCUMENTS

| | | | |
|---|---|---|---|
| 1,025,008 | 4/1912 | Miner | 128/92 D |
| 2,497,626 | 2/1950 | Persall | 128/92 A |
| 4,269,178 | 5/1981 | Keene | 128/69 |

FOREIGN PATENT DOCUMENTS 624615  9/1978  U.S.S.R. .............................. 128/69

*Primary Examiner*—John D. Yasko
*Attorney, Agent, or Firm*—Davis, Hoxie, Faithfull & Hapgood

[57] ABSTRACT

Instrument for spinal treatment comprising a rod with hooks for engaging the vertebrae and means for locking the hooks at selected positions and angles on the rod. A cover is provided to prevent accidental disengagement of the hooks.

5 Claims, 5 Drawing Figures

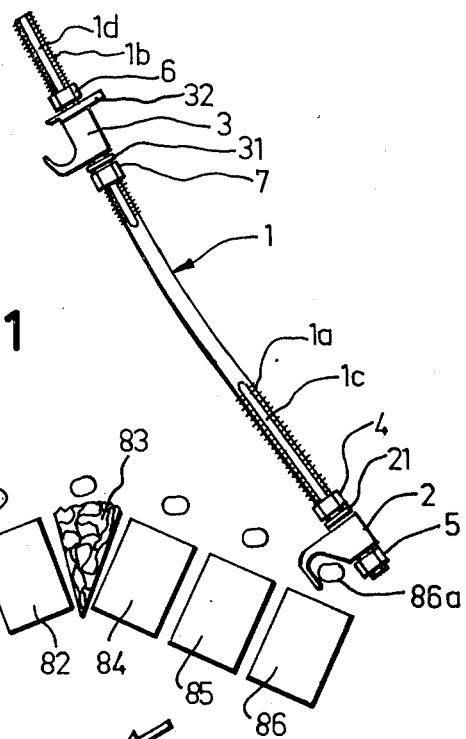
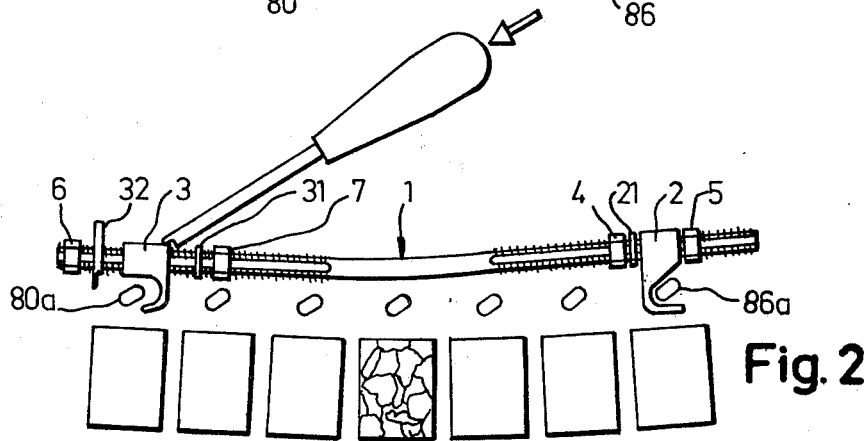
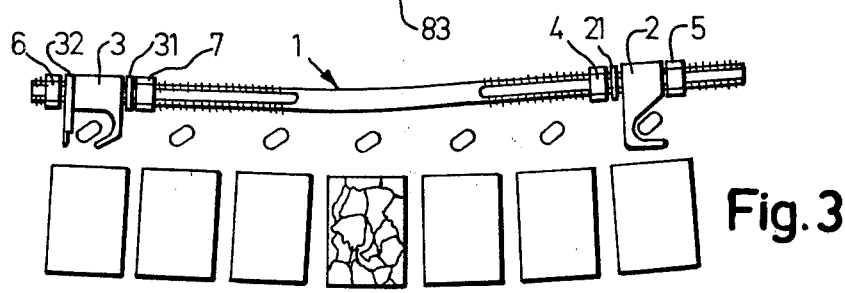
Fig. 1
Fig. 2
Fig. 3

INSTRUMENT FOR TREATMENT OF SPINAL FRACTURES, SCOLIOSIS AND THE LIKE

This invention relates to an instrument for treating spinal injuries and deformities and particularly to a distraction rod which is capable of more secure attachment than distraction rods hitherto available.

For some years certain spinal fractures and scoliosis have been treated with the use of distraction rods, such as the type known as Harrington rods, having hooks for engagement with vertebrae above and below the damaged spinal section. In most instances such hooks are capable of rotation about the rod, and are maintained at the desired angular orientations merely by the frictional resistance of nuts located above and below the hook. Such mechanisms are relatively insecure and under high axial load the hooks tend to swing on the rod, and thus become disengaged from the vertebrae. One proffered solution to this problem is the so-called Moe rod which has a square cross section, to which a matching cross section is provided in the hook openings. This alternative has the disadvantage, however, that when the rod is bent (as it often must be) extreme care must be taken to bend it in the desired plane relative to the plane of the hooks, since no rotational adjustment of the hooks on the rod is possible. Precise bending is often difficult to achieve.

The present invention provides a spinal distraction rod which permits both axial and rotational adjustment of the hooks and locking of the hooks in any desired axial position and rotational orientation.

According to the invention there is provided a device for the treatment of spinal fractures, scoliosis and the like comprising a rod, a hook at each end of the rod, said hooks being movable axially of said rod and rotatable about the axis of said rod and means for fixing said hooks at selected axial positions and for locking said hooks at selected angular positions about the rod axis. In accordance with the invention the rod is threaded at least at each end and nuts are provided above and below each hook for establishing the axial position of the hook on the rod. Further, flats are provided on at least one side of the rod, at each end, and a washer having an aperture or opening corresponding to the cross section of the flattened part of the rod is inserted between each hook and one of the nuts. Locking means in the form of a ribbed surface on the hook and the adjacent surface of the washer makes it possible to lock the hook at a multitude of radial positions on the rod. A cover is provided for at least one of the hooks to avoid undesired disengagement from a vertebrae.

The invention will be described more particularly with reference to the drawings in which:

FIGS. 1 to 3 are views, partly schematic, and partly in side elevation, showing a device according to the invention being applied to treat a fractured spine;

Figure 4:
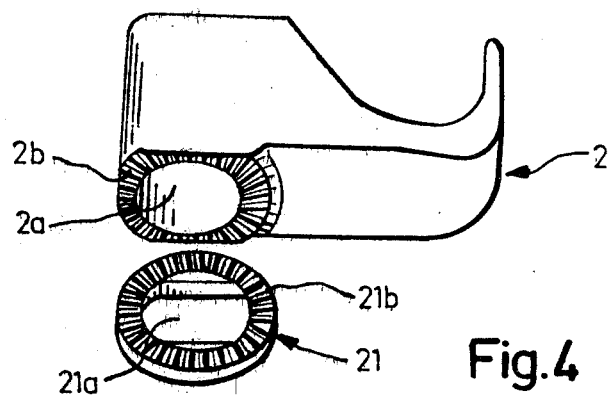
FIG. 4 is a perspective view showing a hook and matching washer for use in a device according to the invention.

Referring to FIGS. 1–3, a device according to the invention comprises a bar or rod 1. The rod has a circular cross section in its central portion, 1e. Flats 1c and 1d are provided on two sides (one side not being visible in the drawings) at each end of the rod and the ends are threaded at 1b and 1a.

Hooks 2 and 3 are provided at each end of the rod. Each of these has a bore hole 2a, 3a which is somewhat larger than the diameter of the rod so that when they are slid over the rod they are free to move axially and to swivel or rotate.

Two nuts 4 and 5 are provided on the rod 1 on either side of hook 2, threaded on the threads 1a. Two other nuts 6, 7 are provided on either side of hook 3, similarly threaded on thread 1b. A washer 21 is interposed between nut 4 and hook 2 and in like manner a washer 31 is interposed between nut 7 and hook 3.

Figure 5:
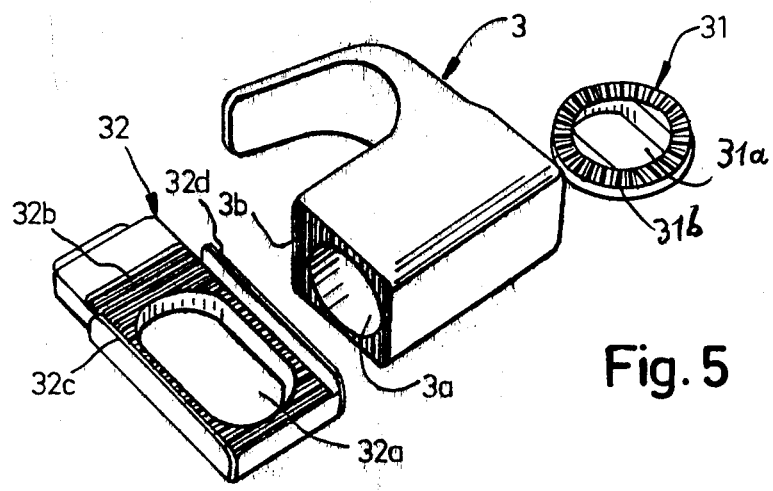
FIG. 5 is a perspective view showing a hook, a cover for the hook and a washer for use in a device according to the invention.

As can be seen best from FIGS. 4 and 5 the openings 21a, 31a, of each washer are shaped to conform to the flats 1c and 1d of the rod 1 so that while the washers can slide along the rod (or the flattened portions thereof) they cannot rotate on the rod. The surfaces of the washers 21 and 31 designed to face the hooks 2 and 3 have radial ribs 21b, 31b. Matching ribs are provided on the surface of the hooks contacting the washers. These are shown at 2b in FIG. 4 for hook 2; the ribs for hook 3 cannot be seen in FIG. 5. The ribs on the hooks and washers are made to nest into one another and are preferably made quite fine. Specifically the ribbing should be fine enough so that a relative rotation of not more than 6° would be sufficient to shift to the next adjacent rib, or trough between ribs. Preferably, the ribbing is such that in a swing of 90° there are about 15 nesting positions.

As shown in FIGS. 1–3, hook 2 is a simple open hook, but hook 3, which would normally be applied at the cranial end of the portion of the spine to be treated, has a cover 32 to close the hook opening and thus to enclose the vertebrae in such manner that it cannot slip out of the hook if the distance between the two points of attachment is shortened, as the result of movement for example.

As shown more particularly in FIG. 5, the cover 32 has a longitudinal slot 32a which enables it to be slid transversely, in a direction perpendicular to the axis of the rod. This is illustrated in FIGS. 1 to 3. In FIGS. 1 and 2 the cover 32 is shown in retracted position and in FIG. 3 in fully closed position. The cover comprises two rubbing strips 32c and 32d on each side which bear against the sides of the hook 3 and prevent the cover from turning. Ribbing 32b is provided on the surface of the cover which faces the hook and matching ribbing 3b (FIG. 5) is provided on the hook surface so that when the cover is pressed against the hook, as is the case when nut 6 is tightenened, the cover can neither slide nor rotate with respect to the hook.

FIGS. 1 to 3 illustrate in a very abbreviated way the manner in which the device is to be used. In FIGS. 1–3 the spinal column is indicated at 80–86 and the injured section at 83. Before application, the rod is bent to the approximate shape it is desired to have that part of the spine assume. This is done by a bending device of known design not shown here. Because the rod is of circular cross section it is possible, if necessary, to bend the bar such that its axis is not wholly within a single plane. Then the hook 2 is positioned on the rod 1 in the correct position axially of the rod and at the correct angle with relation to the rod 1. It is fixed by nuts 4 and 5 and washer 21 and is engaged with the vertebra 86a, in this case three vertebrae below the injury.

The spinal column is then given its approximate natural shape, relieving the injured vertebra, and the hook 3 is engaged with the vertebra 80a. The cover 32 is closed to prevent disengagement and fixed by means of nuts 6 and 7 at the anatomically correct position. Thus the traction necessary from the medical point of view need only be exerted on the section of spine being treated.

It will be understood that many variations are possible in the structures described. For example, in place of a flat on either side of the rod, only one flat might be used; or the flat or flats might be replaced by a groove or grooves with appropriate changes in the shape of the opening of the washers.

What I claim is:

1. An instrument for the treatment of spinal fractures, scoliosis and the like comprising a rod threaded at each end and having a flat at each end, a hook at each end of the rod for engagement with a vertebra, said hooks being movable axially of the rod and rotatable about the rod, and means for securing said hooks at selected positions axially of the rod and angularly about the axis of the rod, said securing means comprising two nuts engaging said threads at each end of the rod, there being a nut on each side of each hook, and a washer at each end of the rod between one of said nuts and its adjacent hook, each washer having a flat engaging the flat on the rod, and radially directed ribs on said washer and on the adjacent face of said hook to prevent rotation of said hooks when said washer is pressed against said hook.

2. The instrument claimed in claim 1 wherein the size of said ribs is selected to permit adjustment of said hook in at least ten positions over a rotational angle of 90°.

3. The instrument claimed in claim 1 wherein at least one of said hooks is provided with closure means to prevent disengagement of the hook from a vertebra.

4. An instrument for the treatment of spinal fractures, scoliosis and the like comprising a rod, a hook at each end of the rod for engagement with a vertebra, said hooks being movable axially of the rod and rotatable about the axis of the rod, securing means, axially adjustable on the rod, for securing said hooks at selected positions axially of said rod and for locking said hooks in selected angular positions about the axis of the rod, and closure means for at least one of said hooks to prevent disengagement of the hook from a vertebra.

5. The instrument claimed in claim 4 wherein the closure means comprises a cover rotatably positioned on said rod, said cover and a surface of the adjacent hook having ribbed surfaces arranged to engage one another to prevent relative rotation of said hook and cover.

* * * * *